United States Patent [19]

Sereboff

[11] Patent Number: 5,565,023
[45] Date of Patent: Oct. 15, 1996

[54] MOISTURE ABSORBING AND FRICTIONAL GRIP ENHANCING COMPOSITION AND METHOD OF FORMING SAME

[75] Inventor: Aaron P. Sereboff, Owings Mills, Md.

[73] Assignee: Fusion All-Sport Grip, Inc., Las Vegas, Nev.

[21] Appl. No.: 558,841

[22] Filed: Nov. 15, 1995

[51] Int. Cl.$^6$ .................................................. C09K 3/14
[52] U.S. Cl. ........................ 106/36; 106/163.01; 252/194
[58] Field of Search ...................... 106/36, 204; 501/109, 501/123; 252/194

[56] References Cited

U.S. PATENT DOCUMENTS

| | | | |
|---|---|---|---|
| 1,851,036 | 3/1932 | Brackett | 106/36 |
| 2,012,259 | 8/1935 | Denman | 523/158 |
| 2,626,219 | 1/1953 | Wagner | 106/36 |
| 2,698,250 | 12/1954 | Leichner | 106/36 |
| 2,987,447 | 6/1961 | Ward | 424/69 |
| 3,035,988 | 5/1962 | Cohen | 427/4 |
| 3,271,170 | 9/1966 | Alhberg | 106/36 |
| 4,563,218 | 1/1986 | Schuler | 106/36 |
| 4,572,690 | 2/1986 | Savanuck | 401/200 |
| 4,800,076 | 1/1989 | Bhat et al. | 424/69 |
| 5,364,464 | 11/1994 | Sereboff | 106/36 |

FOREIGN PATENT DOCUMENTS 591333  2/1978  U.S.S.R. ................... 106/36

*Primary Examiner*—Anthony Green
*Attorney, Agent, or Firm*—Kokjer, Kircher, Bowman & Johnson

[57] ABSTRACT

A moisture absorbing and frictional grip enhancing composition is provided which combines powdered magnesium or calcium carbonate compound particulates and sawdust particulates in a weight percentage ratio approximating 50%–90% by weight of sawdust particulates to the overall composition of weight. The powdered magnesium or calcium carbonate compound particulates are mixed with the sawdust particulates in a dry state to form the overall moisture absorbing and frictional grip enhancing composition which has a spongy feel to the user and optimizes both moisture absorption and frictional gripping of an implement.

6 Claims, No Drawings

MOISTURE ABSORBING AND FRICTIONAL GRIP ENHANCING COMPOSITION AND METHOD OF FORMING SAME

BACKGROUND OF THE INVENTION

1. Field of the Invention

The present invention is a moisture absorbing and frictional grip enhancing composition and method of forming the same. The composition is useful in increasing the frictional grip by a user on an implement while simultaneously providing an interface which is comfortable for the user to grip the implement and absorbs moisture generally in the form of user perspiration to provide the user with additional control of the implement.

In particular, this invention relates to a moisture absorbing and frictional grip enhancing composition formed of two basic components, namely, magnesium or calcium carbonate compound particulates in combination with sawdust particulates. More particularly, this invention directs itself to a moisture absorbing and frictional grip enhancing composition in which sawdust particulates comprise 50%–90% of the composition by weight, and the magnesium or calcium carbonate compound particulates comprise 10%–50% of the composition by weight, when taken with respect to the total composition weight. Still further, this invention directs itself to a moisture absorbing and frictional grip enhancing composition which includes predetermined particulate sizing between 18–300 mesh for the sawdust particulates and 100–400 mesh for the magnesium or calcium carbonate compound particulates. Additionally, this invention relates to a method for forming a moisture absorbing and frictional grip enhancing composition where magnesium or calcium carbonate compound particulates are dry mixed with sawdust particulates in predetermined weight percentage ratios to result in the invention composition.

2. Prior Art

Compositions having as their intended purpose the enhancement of frictional gripping capabilities of users are known in the art. Additionally, compositions having as their intend purpose the absorption of moisture in the form of perspiration from users is also known in the art. The best prior art known to Applicant includes U.S. Pat. Nos. 2,987,447; 3,035,988; 4,563,218; 2,012,259; 2,698,250, 2,626, 219; 4,800,076; 4,572,690, 3,271,170; and 1,214,157.

In different compositions of the prior art such as that shown in U.S. Pat. No. 2,987,447, there are provided hand conditioner compositions to improve the gripping or anti-slip characteristics of user-implement interface in various environments. In such prior art composition there is provided a combination of rosin and talc used in varying amounts. However, although the use of rosin and talc compositions in combination provide for some moisture absorption and frictional enhancement, what is generally left is a tacky type of mixture which adheres to the skin of the user and is difficult to remove. Additionally, such does not provide a spongy type of interface between the user's hand and the implement, which causes a discomfort for the user and results in less control of the implement.

In other prior art compositions, such as that shown in U.S. Pat. No. 3,035,988, there is a rosin type of composition used with ingredients including diatomaceous earth, magnesium oxides and zinc stearates. Such compositions are generally related to talcum powder and once again, does not provide for the advantages of the subject invention concept composition as previously discussed relating to the spongy quality and comfort of the user.

In other prior art compositions such as that shown in U.S. Pat. No. 4,563,218, rosin is provided in quantities up to 50% by weight of a total mixture which is not useful in the subject invention composition since the resulting rosin tackiness and difficulty in removal from the skin of a user is increased.

SUMMARY OF THE INVENTION

A moisture absorbing and frictional grip enhancing composition is provided which includes both first and second predetermined weights of powdered magnesium or calcium carbonate compound particulates and sawdust particulates respectively within a predetermined size range. The total mixture composition is established by mixing the powdered magnesium or calcium carbonate compound particulates with the sawdust particulates in a dry state to form the overall moisture absorbing and frictional grip enhancing composition of the present invention concept.

Further objects, features, and advantages of the present invention over the prior art will become apparent from the detailed description of the drawings which follows.

DETAILED DESCRIPTION OF THE PREFERRED EMBODIMENT

A moisture absorbing and frictional grip enhancing composition and method of forming the same is provided which has advantages over prior compositions relating to comfort, moisture absorbing qualities of the composition, as well as enhanced frictional grip of an implement. The moisture absorbing and frictional grip enhancing composition of the subject invention concept is generally directed for use with any implement which is to be grasped by a user but has particular use in any sport or type of activity where the user wishes to maintain an implement in a tight grip and under conditions where perspiration is a consideration. Such moisture absorbing and frictional grip enhancing compositions may be used for user gripping of implements related to racket sports such as tennis, racquetball, golf as well as weight lifting, baseball or any type of sport where the user wishes to enhance the gripping action of an implement.

The general useful qualities of a moisture absorbing and frictional grip enhancing composition is that such should increase the frictional grip between a user's hand and an implement while simultaneously absorbing the user's perspiration. Additional parameters which are to be optimized directs itself to the feel of the particular composition being used. Where the composition is grainy or particulates are of too large a size, such does not provide for a soft feel with respect to the implement being grasped. Where such a grainy composition is provided, user discomfort may manifest itself in less control of the implement being handled.

Although not oftentimes referred to, friction or grip enhancing compositions should be easily cleansed from the skin of the user subsequent to use which has been a problem area not addressed in some prior compositions.

There have been many different types of compositions which have used rosin to aid in gripping however, such systems have been found to provide a tacky feeling to the user's hands and although providing a high coefficient of friction, such does not materially aid in absorbing perspiration of the user and is not easily removable from the hands. Additionally, talcum powder has been placed in combination with rosin to provide an absorbing type of system but such composition only absorbs perspiration to a low extent while maintaining the tacky residue on the hands of the user.

Sawdust has been used for some types of liquid absorbing capabilities and is known to have been used in barns and other areas where liquid absorption is necessary however, the sawdust used in these types of environments is generally formed of large shavings, sometimes in the size range of 0.5"–1" in length. Such sawdust type particles are substantially rigid formations which cannot be used by a user grasping an implement due to the fact that the shavings are cut into the hand and cause discomfort. Additionally, large sized sawdust shavings do not provide the frictional enhancement necessary in gripping an implement.

The inventor has found that by mixing a first predetermined weight of a compound which includes an alkaline earth metal carbonate element, such as magnesium or calcium carbonate, in powdered form, and a second predetermined weight of sawdust particulates, the moisture absorbing and frictional grip enhancing resulting composition has great advantages over that which is known. The first predetermined weight of the compound containing alkaline earth metal carbonate components in particulate form and the second predetermined weight of sawdust particulates are mixed in a dry state to form the overall moisture absorbing and frictional grip enhancing composition of the subject invention concept.

The combination of particulates used in the subject invention composition has a combined effect which is both greatly different and not evident, as compared to the effect of either of the particulates alone. The powdered magnesium or calcium carbonate compound particulates adsorb to the sawdust particulates in the mixed and dry state and the resulting composition becomes spongy in texture prior to use. The powdered magnesium or calcium carbonate compound particulates and the sawdust particulates are mixed together in the dry state and then allowed to settle in a substantially dry environment for a period of time which allows the spongy quality to emerge.

When used for grasping an implement, the composition of the subject invention system increases the frictional grip of the user while at the same time providing a soft and highly perspiration absorbing composition. Additionally, subsequent to use, any residue is easily washed from the skin of the user by merely passing an aqueous solution over the user's skin with the subject composition being easily removed.

The inventor discovered that a singular composition of sawdust particulates does provide some moisture absorbing and frictional grip enhancing features. However, the sawdust particulates, even in an extremely small size range, were found to present hardened point forces to the skin of the user and cause discomfort. Additionally, the frictional gripping of the implements was not found to be greatly enhanced over that of no composition being used, although there was some increase in the frictional qualities observed. Thus, the mere use of the sawdust particulates did allow for a moisture absorbing composition but did not greatly increase the frictional qualities and further caused discomfort to the users when the implement did slip and there was a displacement of the particulates contiguous the skin of the user.

Preferably, the magnesium or calcium carbonate compound used in the composition of the present invention is used in the form of a powder. The magnesium or calcium carbonate compound used comprises particulates preferably in the size range of approximately 100–400, and most preferably between 200–320 mesh size when used in combination with sawdust particulates in the approximate size range between approximately 18–300, and most preferably about 30–120 mesh.

The sawdust preferably comprises pine or hardwood particulate.

Additionally, the size range of the magnesium or calcium carbonate compound particulates were found to be advantageous when slightly less than or substantially equal to the size range of the sawdust particulates. The benefits of the composition appear to be greatest when the sawdust particulate sizes are greater than the particulate sizes of the magnesium or calcium carbonate compound particulates.

Various percentage ranges were used for the weight of the overall mixture of the sawdust particulates and the magnesium or calcium carbonate compound particulates in combination. Where too great an amount of magnesium or calcium carbonate compound particulates were used, a clumping effect may occur with the mixture appearing to be nonhomogeneous. This result may lower the moisture absorption capabilities when the magnesium or calcium carbonate compound particulate weight percentage is increased over 50% of the total mixture weight. Additionally when the sawdust particulate weight percentage is increased to over 90% of the total mixture composition, the spongy texture is reduced with an increase of discomfort to the user. The exact percentage ratios may vary due to the fact that discomfort levels between different users varies and trying to quantify the optimum percentage ranges is extremely difficult and to a certain extent individualistic.

With a weight percentage of within the approximate range of 50%–90% of sawdust particles to 10%–50% of magnesium or calcium carbonate compound particulates, the overall composition maintains a spongy type of texture and provides a comfort level in useful operation. The optimal composition appears to be approximately 90% by weight of sawdust particulates to 10% by weight of magnesium or calcium carbonate compound particulates to the total weight of the composition.

When the percentage of the sawdust particulates drops below 50% by weight of the total mixture, the particulates may cause discomfort on the skin of the user, although still provide high liquid absorption. When the sawdust particulate weight percentage is above approximately 90% of the total weight mixture, the magnesium or calcium carbonate compound particulates may not provide sufficiently spongy total mixture and once again may result in a higher discomfort level among users gripping implements.

Further, this invention concept provides and contemplates a method of forming the moisture absorbing and frictional grip enhancing composition. Initially, a first predetermined weight of powdered magnesium or calcium carbonate compound particulates is established in a container. A second predetermined weight of sawdust particulates is provided in a second container with both of the first and second predetermined weights of respective powdered magnesium or calcium carbonate compound particulates and sawdust particulates being in the dry state.

The particulates are established within the above-referenced size dimensions and then mixed in a third container and agitated for thorough mixing. The combined mixture is then allowed to settle in a dry state for a period of time which has been in the region of 24 hours. The resulting composition is found not to be gritty or tacky in nature but rather to be spongy and provides a comfortable interface between the hand of a user and the implement which is being gripped.

The first and second predetermined weights of particulates are mixed in the third container within a weight ratio of an approximating range of 50%–90% of sawdust particles to 10%–50% magnesium or calcium carbonate compound particulates.

While in the preferred embodiment the composition includes calcium or magnesium carbonate, as set forth above, the composition may include any number of compounds which include an alkaline earth metal and carbonate component. The composition may even include a mixture of several of such elements, such as both magnesium and calcium carbonate particulates in combination with the sawdust. The calcium or magnesium carbonates maybe manufactured, or obtained from naturally occurring deposits such as calcite, limestone, etc.

Other materials which may be useful in combination with the sawdust to provide a useful composition in accordance with the present invention include magnesium silicate (as disclosed in my prior patent, U.S. Pat. No. 5,364,464), calcium silicate, and other compounds including oxides and silicates of aluminum, iron, and alkaline earth metals, such as those known as feldspar, mica, portland cement, etc.

The resulting mixture produced has been found to have a reasonable shelf life and is accepted by users as an improvement over prior gripping compositions.

It will be understood that the above described arrangements of apparatus and the method therefrom are merely illustrative of applications of the principles of this invention and many other embodiments and modifications may be made without departing from the spirit and scope of the invention as defined in the claims.

I claim:

1. A moisture absorbing and frictional grip enhancing composition comprising:

an alkaline earth metal carbonate particulates; and sawdust particulates;

said alkaline earth metal carbonate particulates mixed with said sawdust particulates in a dry state to form said moisture absorbing and frictional grip enhancing composition.

2. The composition of claim 1, wherein said alkaline earth metal carbonate particulates comprise calcium carbonate.

3. The composition of claim 1, wherein said alkaline earth metal carbonate particulates comprise magnesium carbonate.

4. The composition of claim 1, wherein said alkaline earth metal carbonate particulates have a particle size within a mesh size of about 100–400.

5. The composition of claim 1, wherein said sawdust particulates have a particle size of between about 18–300 mesh size.

6. The composition of claim 1, wherein said sawdust particulates comprise between about 50%–90% of the total weight of the composition.

* * * * *